(12) United States Patent
Park

(10) Patent No.: US 7,554,088 B2
(45) Date of Patent: Jun. 30, 2009

(54) METHOD FOR POSITRON EMISSION IMAGING

(76) Inventor: Chul Hi Park, 1285 Altamead Dr., Los Altos, CA (US) 92024

( * ) Notice: Subject to any disclaimer, the term of this patent is extended or adjusted under 35 U.S.C. 154(b) by 211 days.

(21) Appl. No.: 11/539,633

(22) Filed: Oct. 7, 2006

(65) Prior Publication Data

US 2007/0138396 A1 Jun. 21, 2007

Related U.S. Application Data

(60) Provisional application No. 60/726,557, filed on Oct. 13, 2005.

(51) Int. Cl.
*G01T 1/161* (2006.01)
(52) U.S. Cl. .............................. 250/363.04; 250/363.03
(58) Field of Classification Search ............ 250/363.03, 250/363.04, 363.1, 369
See application file for complete search history.

(56) References Cited

U.S. PATENT DOCUMENTS 4,559,597 A * 12/1985 Mullani .................... 600/407
4,743,764 A * 5/1988 Casey et al. ............ 250/363.03
5,103,098 A * 4/1992 Fenyves ...................... 250/368
5,936,247 A * 8/1999 Lange et al. ........... 250/363.03

OTHER PUBLICATIONS

American Cancer Society, "Colorectal Cancer Facts & Figure, Special Edition 2005,", 2005, American Cancer Society, Inc.
R.H. Huebner et al,. "A Meta-Analysis of the Literature for Whole-Body FDG PET Detection of Recurrent Colorectal Cancer," The Journal of Nuclear Medicine, vol. 41, No. 7, Jul. 2000, pp. 1177-1189, University of California, Los Angeles.

* cited by examiner

*Primary Examiner*—David P Porta
*Assistant Examiner*—Mark R Gaworecki

(57) ABSTRACT

A method for positron emission imaging is described. A portion of an imaging subject containing a radiopharmaceutical labeled with positron emitting radionuclide is disposed between and in close proximity with a pair of gamma detectors in opposing positional relationship. Pairs of coincidence gamma rays emitted from positron annihilation events are recorded by the pair of gamma detectors. The gamma detectors are scanned over and across an area of interest of the imaging subject while their position information is recorded. The recorded gamma ray events at each scan interval are used to represent two dimensional image of positron emitting radionuclide distribution within the imaging subject.

17 Claims, 4 Drawing Sheets

METHOD FOR POSITRON EMISSION IMAGING

BACKGROUND OF THE INVENTION

This invention relates generally to a method for medical examination, in particular, radiographic imaging of organs using positron emitting radiopharmaceuticals.

The American Cancer Society estimates that in 2005 about 145,290 people will be diagnosed with colorectal cancer and that about 56,290 people will die of the disease in the United States. [American Cancer Society. *Colorectal Cancer Facts & Figure, Special Edition* 2005. Atlanta: American Cancer Society, 2005.] The great majority of these cancers and deaths could be prevented by wider use of established screening tests. Yet, cancers of the colon and rectum combined are the third most common type of cancer and the second most common cause of cancer death in the United States. Screening can prevent many cases of colorectal cancer because most colorectal cancers develop from adenomatous polyps. Polyps are non-cancerous growths in the colon and rectum. Detecting polyps through screening and removing them can actually prevent cancer from occurring.

Colonoscopy is the most effective method for screening colorectal cancer. In a screening colonoscopy procedure a physician visually examines the full length of colon for adenomatous polyps on the wall, which may be removed during the same procedure. Although colonoscopy is most sensitive among various screening methods for the detection of polyps and cancers, there is some probability that these abnormalities are missed especially when they are small or of shapes that are difficult to distinguish.

While colonoscopy screens colorectal cancer by seeking out morphological changes in the wall of colon, Positron Emission Tomography (PET) presents an opportunity to detect colorectal and other cancers based on their distinctive physiological signatures even at a stage of cancer development too early for morphological changes to be visually recognizable. PET is a radionuclide imaging method in which a positron emitting radiopharmaceutical such as [$^{18}$F] fluoro-2-deoxy-D-glucose (FDG) is used to visualize metabolic processes in a patient. FDG is a radioactive analog of glucose, which is phosphorylated and trapped within cells. After a patient receives a dose of FDG he or she is examined with a scanner that is capable of detecting pairs of correlated gamma rays resulting from annihilations of positrons emitted from $^{18}$F nuclei. The coincident gamma rays travel along a line in opposite directions and are detected by a pair of opposing detectors in the PET scanner. The data collected from the scanner are used to reconstruct the distribution or three dimensional image of metabolic byproduct of FDG in a patient body. PET, using FDG (FDG-PET) as a tracer of tumor glucose metabolic activity, is an accurate non-invasive imaging technology which probes physiological functions of tissue and organ rather than their structures or morphologies. The increased rate of glycolysis in neoplastic or cancer cells, independent of the oxygen concentration present, has been previously reported. [O. Warburg, "On the origins of cancer cells," Science, Vol. 123, 309-314 (1956)].

FDG-PET has been established as an effective tool for diagnosis of recurrent or metastatic colorectal cancer. The sensitivity (probability of correctly identifying a lesion) and specificity (probability of correctly identifying a non-lesion) of FDG-PET for the detection of recurrent disease have been reported as approximately 95% and 76%, respectively. [R. H. Huebner, K. C. Park, J. E. Shepherd, J. Schwimmer, J. Czernin, M. Phelps, S. Gambhir, "A meta-analysis of the literature for whole-body FDG PET detection of recurrent colorectal cancer," Journal of Nuclear Medicine, Vol. 41, 1177-1189 (2000)] However, the sensitivity of PET for pre-malignant colon lesions and early stage colorectal cancer is very limited. This is especially true for flat, pre-malignant lesions, and protruded, pre-malignant lesions smaller than 3 cm and colon cancers smaller than 2 cm. [S. Friedland, R. Soetikno, M. Carlisle, A. Taur, T. Kaltenbach, G. Segall, "18-Fluorodeoxyglucose positron emission tomography has limited sensitivity for colonic adenoma and early stage colon cancer," Gastrointestinal Endoscopy, Vol. 61(3), 395-400 (2005)]

This sensitivity limitation of PET is primarily attributable to poor spatial resolution of PET scanner and insufficient amount of positron annihilation data recorded in a typical imaging procedure for reconstructing a clinical image. A conventional PET typically yields reconstructed images with a spatial resolution of 8-15 mm, depending on the injected dose, imaging time, and intrinsic resolution of the scanner. Gamma ray pairs produced in positron annihilations in the field of view (FOV) must travel through intervening tissues to reach a pair of opposing detectors in a ring of detectors of PET scanner which is positioned outside and surrounding a patient or an imaging subject. A fairly large fraction of gamma rays is attenuated through absorption or scattered away from initial line of flight during the passage through intervening tissue. Among those gamma photons successfully leaving the patient body undisturbed only a small fraction falls within the limited geometric acceptance of PET scanner and is ultimately recorded. The loss of gamma rays through attenuation and scattering, and the limited geometric acceptance of PET scanner are two of the most significant factors limiting the amount of positron annihilation events recorded in a typical PET imaging procedure. Because of these inefficiencies inherent to a conventional PET a prolonged imaging time or a large dose of FDG is usually required to produce a clinical image of acceptable diagnostic quality.

A conventional PET also suffers from a large number of uncorrelated gamma rays ("singles"). The singles are recorded when one of gamma ray pairs emitted in positron annihilation events goes undetected by PET scanner for one reason or another, e.g., attenuation and scattering within tissues. A pair of singles can fake as a genuinely correlated pair of gamma rays (a random coincidence event) and enter the detection stream in spite of measures designed to discriminate against such occurrences. These random coincidence events incur a significant scanner dead time during which PET scanner remains ineffective and typically show up in the image as a burring background and reduce image contrast lowering diagnostic quality of the image. Similar, undesirable effects on the image result when one or both of correlated gamma rays from a positron annihilation event experiences a scatter in the patient body and deviates from its original line of flight before being detected and recorded as a genuine, prompt positron annihilation event (a scatter coincidence event).

A conventional PET is also one of the most expensive medical imaging modality due to the high price of a PET scanner, which is an important factor limiting wider spread use.

Uniqueness of colon anatomy presents an opportunity to implement the positron emission imaging in entirely different ways than a conventional PET. Colon is an elongate tubular organ with a thin, pliable wall, which can be regarded as a thin sheet of tissue rolled into a tube. The wall of entire length of colon is accessible from inside in minimally invasive manner through anus. This allows a pair of gamma detectors to be positioned with their radiation sensitive faces facing each other, and sandwiching and making contacts with a portion of folded colon wall of a small volume. The gamma detector pair is scanned over and across the colon wall area of interest during which the position of the gamma detector pair with respect to a fixed origin and coincidence gamma rays from positron annihilation events are recorded. The information thus obtained can be utilized to produce a planar image of the distribution of positron emitting radiopharmaceutical in the area of colon wall.

The proximity of the opposing pair of gamma detectors with an imaging subject provides many advantages. Because of the small volume covered by the FOV of the gamma detector pair the attenuation and scattering of gamma rays from positron annihilation events within the FOV are largely negligible. Because of the small size of gamma detectors, singles and random coincidence event rates contributed by tissues surrounding the gamma detector pair are very low and the detector dead time is negligible. The lack of attenuation and detector dead time of the present imaging method leads to a significant increase in the sensitivity for detecting true coincidence events resulting from positron annihilation events. Increase in sensitivity can be advantageously utilized to reduce imaging time and FDG dose, and to improve diagnostic quality of image. The proximity of gamma detectors with the imaging subject allows the spatial resolution of the imaging system to be primarily determined by the intrinsic resolution of the gamma detector pair, which in turn is highly dependent on the geometry of individual gamma detector and relative positional relationship of the gamma detector pair. In contrast the spatial resolution of PET is significantly influenced by factors other than the intrinsic resolution of the PET scanner, which is often difficult to control. Due to inherent simplicity the price of a new imaging system incorporating the present imaging method will be much lower than that of a conventional PET system.

In the past planar imaging methods utilizing positron emitting radiopharmaceuticals have been used to study the transport of radiopharmaceutical in a small imaging subject [S. Seigel, J. J. Vaquero, L. Aloj, J. Seidel, E. Jagoda, W. R. Gandler, W. C. Eckelman, M. V. Green, "Initial results from a PET/Planar small animal imaging system, " IEEE Transactions on Nuclear Science, Vol. 46, No. 3, 571-575 (1999)] and to perform a dynamic study of radioactivity in arterial blood. [S. Shokouhi, S. Stoll, A Villanueva, P. Vaska, D. Schlyer, C. Woody, B. Yu, P. O'Connor, J. Pratte, V. Radeka, N. volkow, J. Fowler, "A non-invasive LSO-APD blood radioactivity monitor for PET imaging studies, " IEEE Transactions on Nuclear Science, Vol. 50, 1447-1461 (2003); S. Rajeswaran, D. L. Bailey, S. P. Hume, D. W. Townsend, A. Geissbuhler, J. Young, T. Jones, , "2D and 3D imaging of small animals and the human radial artery with a high resolution detector for PET, " IEEE Transactions on Nuclear Science, Vol. 11, No. 3, 386-391 (1992)] In these imaging methods the detectors are positioned outside a live imaging subject away from the main regions of interest and therefore there still exist some of drawbacks found in conventional PET.

BRIEF SUMMARY OF THE INVENTION

Embodiments of the present invention relate to one or more of the following: (1) a method for positron emission imaging capable of delivering clinical images of greater spatial resolution than that of prior art positron emission imaging method, (2) a method for positron emission imaging capable of providing a larger amount of positron annihilation event data than prior art positron emission imaging method, (3) a method for positron emission imaging capable of delivering clinical images with smaller background noise than prior art positron emission imaging method, (4) a method for positron emission imaging capable of producing a clinical image in shorter time and reduced patient radiation dose than prior art positron emission imaging method, and (5) a method for positron emission imaging that costs less to produce a clinical image than prior art positron emission imaging method.

One embodiment of the present invention is directed to a method for imaging a body part. A method for imaging a body part utilizes a pair of gamma detectors disposed about and in an adjacent relationship with the body part so as to detect coincident gamma ray pairs generated by positron annihilation events occurring within the body part, each detector capable of detecting gamma rays emitted by a positron emitting radiopharmaceutical infiltrated into the body part. The method includes scanning the detector pair across and over the body part; detecting coincident gamma ray pairs generated by positron annihilation events occurring within the body part at each scan interval; determining position coordinates of the detector pair with respect to a fixed origin at each scan interval; utilizing the number of gamma ray pairs detected at each scan interval and the determined coordinates to generate an image indicative of the distribution of positron emitting radiopharmaceutical within the body part.

The method of the present embodiment has a number of advantages over a conventional positron emission imaging method, i.e., PET. The present method provides a substantial increase in the total amount of positron annihilation event data that can be used to produce a clinical image. The present method also provides significantly improved spatial resolution, which helps expand the diagnostic range of clinical images by making smaller features more discernible. An imaging system implementing the present method will be significantly cheaper than a conventional positron imaging system leading to wide spread use of positron imaging method. Unlike PET, the present method does not require reconstruction step to extract clinical image from recorded data simplifying imaging process and further lowering imaging cost.

These and other features, aspects, and advantages of the present invention will become better understood with regard to the following detailed description, appended claims, and accompanying drawings.

BRIEF DESCRIPTION OF THE DRAWINGS

The following exemplary figures are provided to supplement the description below and more clearly describe the invention. In the figures, like elements are generally designated with the same reference numeral for illustrative convenience and should not be used to limit the scope of the present invention.

DETAILED DESCRIPTION OF THE INVENTION

Figure 1A:
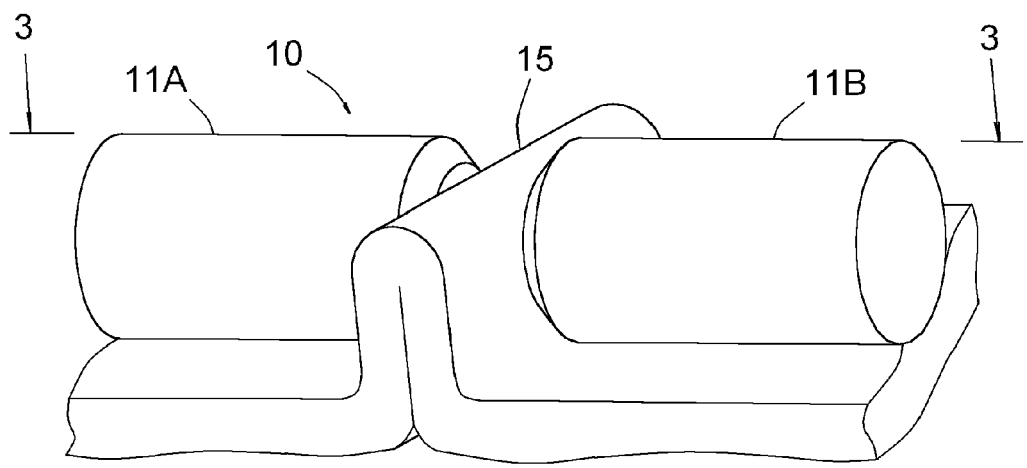
FIG. 1A schematically shows a perspective view of an imaging configuration where a portion of colon wall is disposed between a pair of gamma detectors.
Figure 1B:
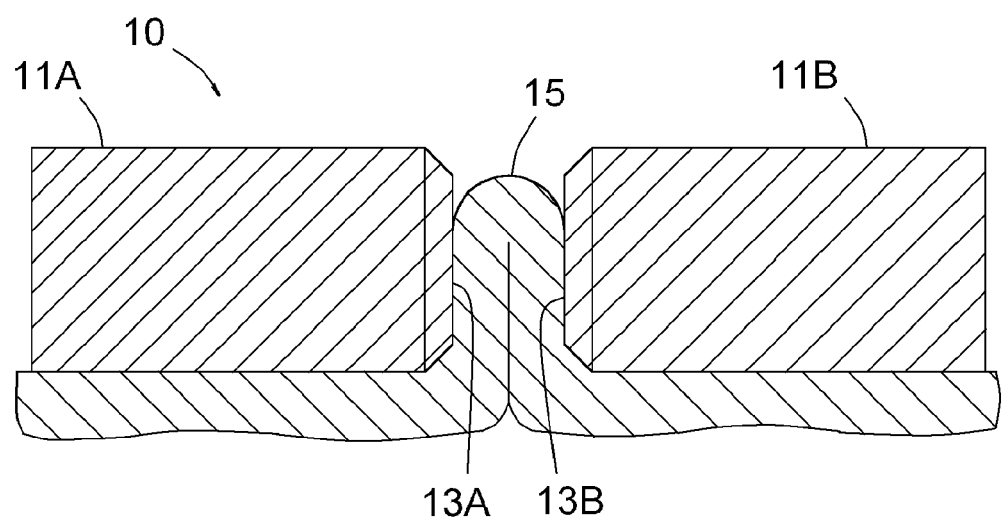
FIG. 1B is a sectional view of the gamma detectors and the colon wall taken along line 3-3 of FIG. 1A.
Figure 2A:
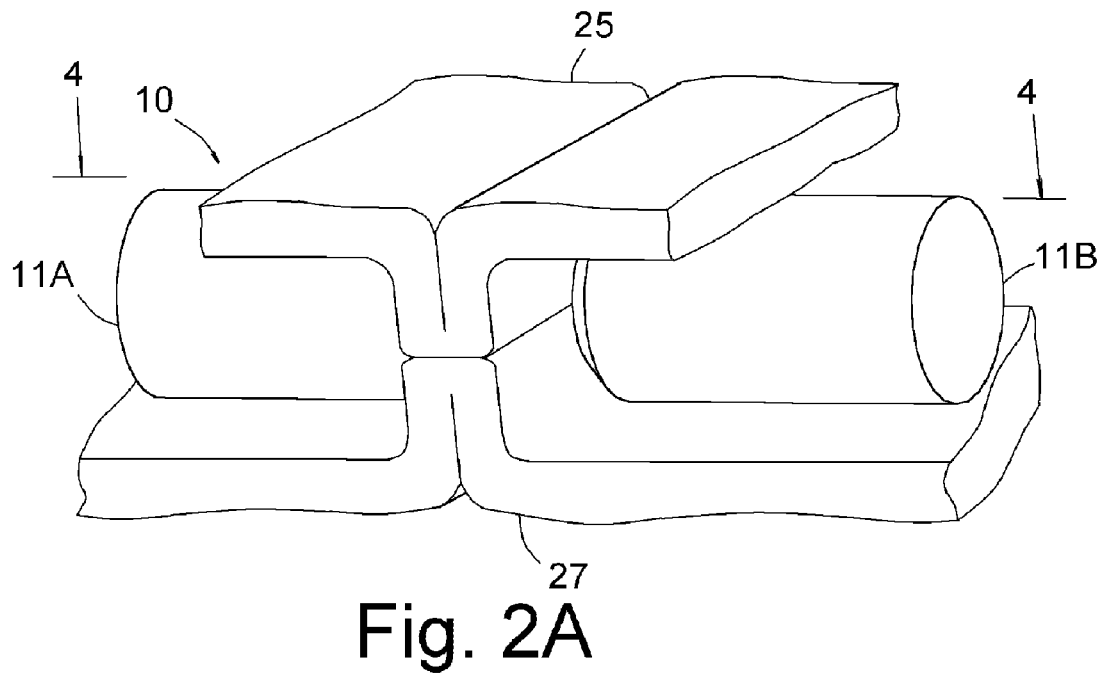
FIG. 2A schematically shows a perspective view of an alternative imaging configuration where portions of colon wall disposed between a pair of gamma detectors.
Figure 2B:
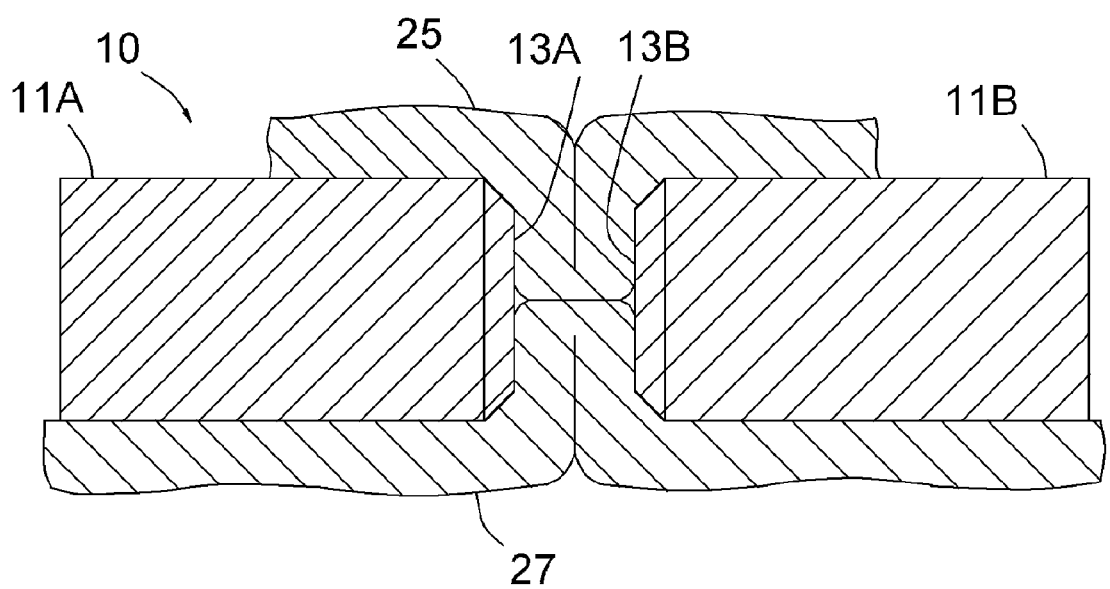
FIG. 2B is a sectional view of the gamma detectors and the colon wall taken along line 5-5 of FIG. 2A.

Referring to FIG. 1A-2B, a coincidence gamma detector assembly 10 comprises a pair of gamma detectors 11A, 11B in opposing positional relationship so that their radiation sensitive faces 13A, 13B confront each other. A radiation sensitive face is a side of the gamma detector where most of gammas originating from the FOV of coincidence gamma detector assembly 10 enter the gamma detector. Gamma detectors 11A, 11B may be any kind of spectroscopic detectors that are suitable for the detection of gamma rays of energies in the range, for example, between 100 keV and 1 MeV, typically found in the medical imaging field utilizing positron emission radiopharmaceuticals and capable of accurately recording the time of detection. For example, the gamma detectors of the present invention may comprise scintillation crystals coupled to visible photon detectors. Suitable scintillation crystals may include Cesium Iodide (CsI(Tl)), Bismuth Germinate (BGO), Lutetium Oxyorthosilicate (LSO), Lutetium Yttrium Orthosilicate (LYSO). Cerium-doped Gadolinium Silicate GSO, Sodium Iodide (NaI(Tl)) and suitable photon detectors may include photomultiplier tube, silicon diode and avalanche photodiode. Alternatively, the gamma detectors may comprise a solid state gamma detector such as Cadmium Zinc Telluride (CZT), Cadmium Telluride (CdTe), Germanium (Ge), Silicon (Si) and Mercuric Iodide (HgI). Gamma detectors 11A, 11B may be configured to be position-sensitive having an equal number of multiple detection channels, each detection channel functioning as a gamma detector independent from each other, so as to provide positional information in addition to spectroscopic and temporal information of detected gamma rays. Gamma detectors 11A, 11B may be of dimensions suitable for use in a position inside a patient such as colon or other digestive tract. For example, the transverse dimension parallel to radiation sensitive faces 13A, 13B may be approximately between 0.3 cm and 1.5 cm and the longitudinal dimension may be between 0.5 cm and 2 cm. Gamma detectors 11A, 11B may include radiation shielding on all sides other than radiation sensitive faces 13A, 13B to suppress the detection of gamma rays originating from regions outside the FOV. The radiation shielding materials may include tungsten, lead and molybdenum. The thickness of the radiation shielding may be between 0.1 mm and 5 mm.

A pair of back-to-back gamma rays resulting from a positron annihilation event in colon wall or a body part under examination is detected by a detector pair 11A, 11B or by a pair of detection channels in directly opposing positional relationship, one in gamma detector 11A and the other in gamma detector 11B. To be recorded as a genuinely correlated pair of gamma rays from a positron annihilation event the detected gamma rays must pass two selection conditions: (1) the two gamma rays should be detected within a predetermined coincidence resolving time, for example, $10^{-8}$ second; (2) energy of each gamma ray should fall within a predetermined energy window centered around 511 keV, which is the precise energy of each gamma ray emitted in a positron annihilation event or be larger than a minimum threshold, for example, 350 keV. Since a gamma ray pair from a positron annihilation event travels back-to-back in a line of response it is unlikely that a pair of gammas originating from a positron annihilation event occurring outside the FOV of a pair of gamma detector or a pair of detection channels get recorded.

Still referring to FIG. 1A-2B, in an imaging configuration of the method of the present invention a portion of folded colon wall 15 or any other body part to be imaged is positioned between opposing radiation sensitive faces 13A, 13B of gamma detectors 11A, 11B of coincidence gamma detector assembly 10. In an alternative imaging configuration two approximately equal portions of folded colon wall 25, 27 may be positioned between opposing radiation sensitive faces 13A, 13B. In order to produce an image or, equivalently, to map positron emitting radionuclide distribution in an area of colon wall, coincidence gamma detector assembly 10 is scanned in raster pattern over and across the area of interest in predetermined discrete steps while maintaining, at every scan interval, the positional relationships between pair of gamma detectors 11A, 11B and a portion or portions of colon wall under examination as shown in FIG. 1A or FIG. 2A. Alternatively, coincidence gamma detector assembly 10 may be scanned continuously while the parameters of scanning motion are carefully controlled. During each scanning step, the position of coincidence gamma detector assembly 10 with respect to a fixed origin is recorded along with the number of coincidence gamma events recorded. In case of continuous scan, the scan speed is recorded as a function of time, from which the position information of coincidence gamma detector assembly 10 with respect to a fixed origin may be derived. The dimension of a scan interval may be chosen to approximately coincide with the intrinsic spatial resolution of the coincidence gamma detector assembly.

A suitable positioning device (not shown) may be employed to facilitate the disposition of a portion or portions of colon wall between the radiation sensitive faces of a gamma detector pair.

Using the position information of gamma detector assembly 10 and number of gamma ray pairs detected during scanning one can generate an image representative of positron emitting radionuclide within an area of colon wall or the imaging subject.

Figure 3:
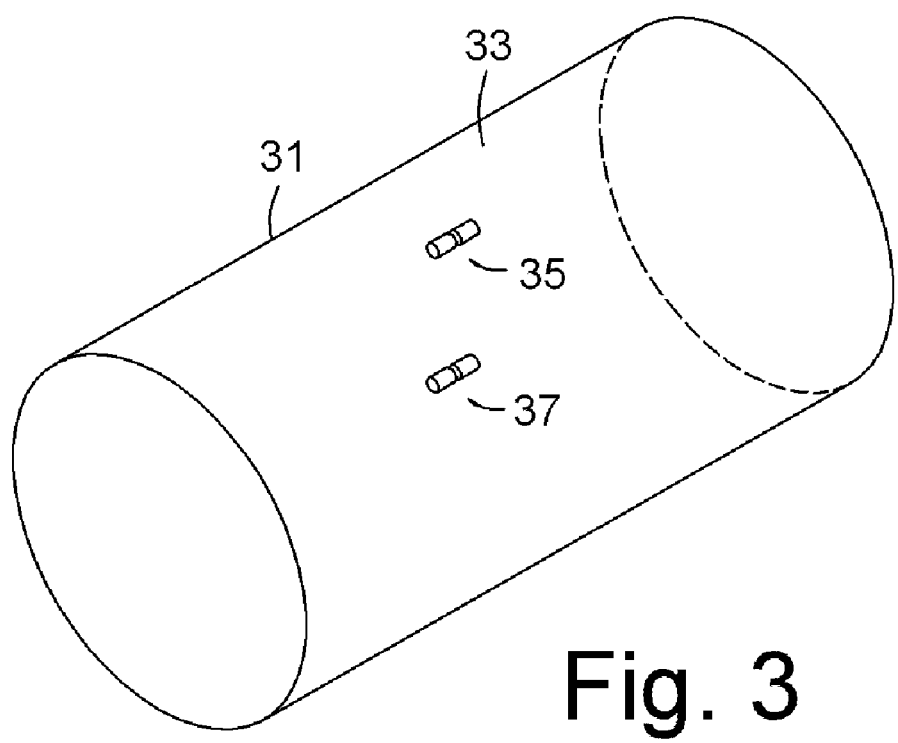
FIG. 3 schematically shows a perspective view of a water phantom used to simulate the detector responses with a detector pair located at and off the center of the phantom.
Figure 4:
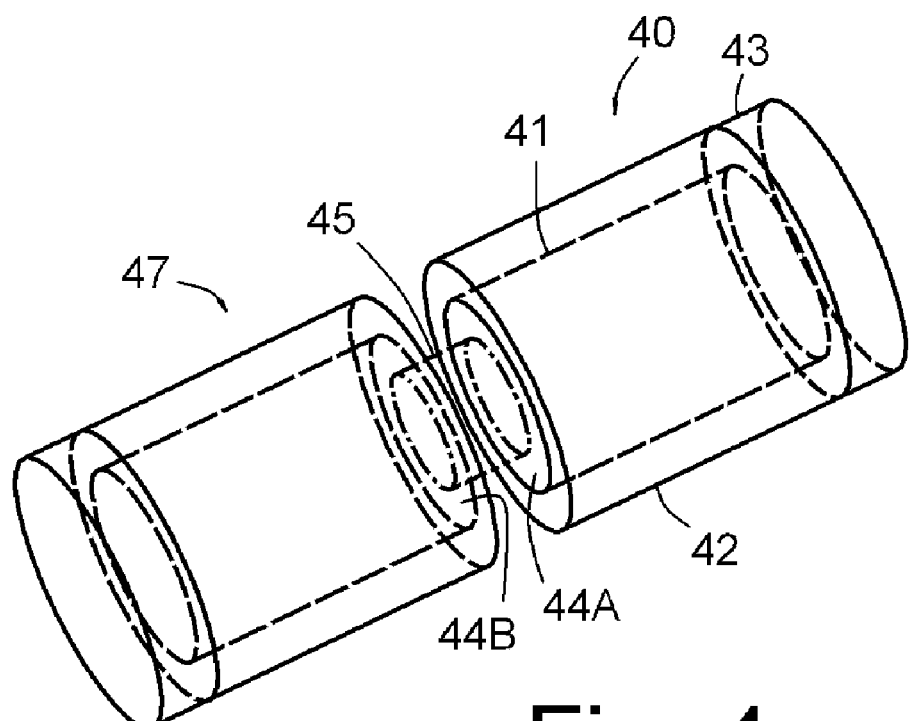
FIG. 4 schematically shows an enlarged perspective view of a pair of gamma detectors and a FOV between them.

A numerical simulation study based on EGS4 Monte Carlo code [W. R. Nelson, H. Hirayama, and D. W. O. Rogers, "The EGS4 Code System," SLAC-265, Stanford Linear Accelerator Center (December 1985)] was carried out to understand the performance characteristics of the imaging method of the present invention. Shown in FIG. 3 is a cylindrical phantom 31 of 20 cm in diameter and 50 cm in length filled with water 33 containing uniform radioactivity concentration of 0.5 µCi/mL used to simulate an environment where positron imaging based on the method of the present embodiment is likely to be performed. Also shown in FIG. 3 are pairs of cylindrical gamma detectors comprising gamma detector assemblies 35, 37 positioned in two different locations, at and off the center of phantom 31 with the symmetry axis in parallel orientation with that of the phantom and with their radiation sensitive faces separated by 0.4 cm and confronting each other. Referring to FIG. 4, a gamma detector 40 is assumed to comprise a cylindrical scintillation crystal 41 of 1 cm in diameter and 1.5 cm in length made of BGO with 0.1 cm thick tungsten radiation shielding 42 surrounding the side of the cylindrical crystal and impenetrable radiation shielding 43 at the bottom face opposite a radiation sensitive face 44A. The gamma detector 40 may have different dimensions in other implementations.

Figure 5A:
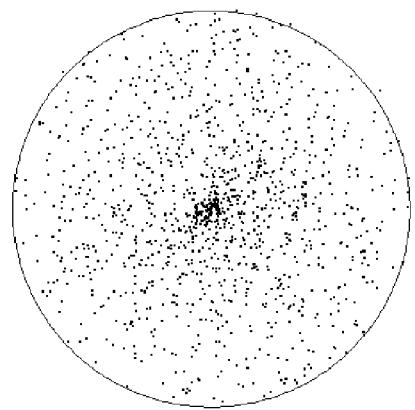
FIGS. 5A and 5B show axial and side views, respectively, of the distribution of locations of origins of uncorrelated gamma rays where a detector pair is located at the center of the water phantom.
Figure 5B:
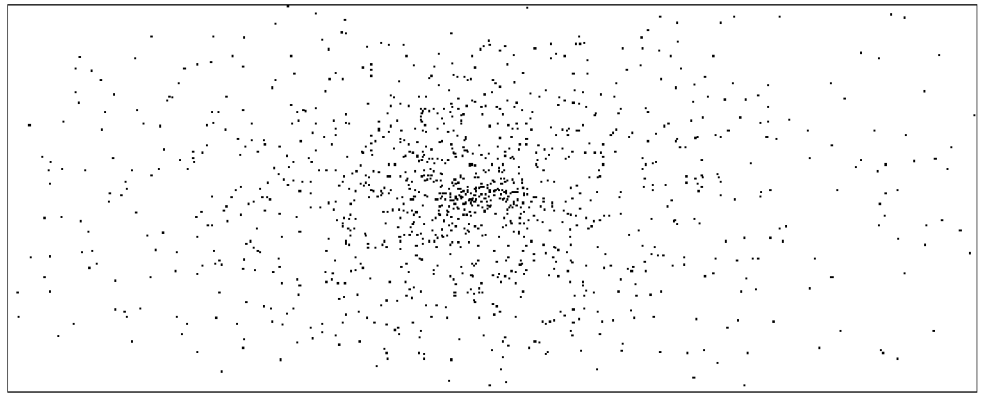

Shown in FIGS. 5A and 5B are axial and side views of the distribution of locations of origins of singles detected by a gamma detector of coincidence gamma detector assembly 37, shown in FIG. 3, located at the center of the phantom. Most of the singles events are contributed by positron annihilation events from the region outside the FOV of coincidence gamma detector assembly 37. A large fraction of singles is secondary gamma rays created when primary gamma rays from positron annihilation events undergo scattering. These secondary gamma rays generally have lower energies than those of primary gamma rays and enter the gamma detectors mostly through sides other than radiation sensitive faces, where radiation shielding can be freely applied. By adding even relatively light radiation shielding on these sides such as tungsten or lead plate of thickness less 0.2 cm, fairly substantial reduction of singles can be achieved.

For a detector pair at the center of the phantom the detection rate normalized to the radioactivity per unit volume for singles with measured energies greater than 350 keV is approximately 90,000 (counts/second)/($\mu$Ci/mL). For a detector pair off the center of the phantom by 8.5 cm in radial direction, the singles detection rate is approximately 45% smaller mainly due to difference in average distance between the gamma detectors and positron annihilation locations. Assuming $10^{-8}$ second for the width of coincidence resolving time this rate corresponds to approximately 162 (counts/second)/($\mu$Ci/mL) of random coincidence events detected by coincidence gamma detector assemblies 35, 37, which is calculated by a well known formula $2\tau C_s^2$, where $\tau$ is the coincidence resolving time and $C_s$ is the singles detection rate.

In real imaging application the presence of a local hot spot of radioactivity, such as the bladder, in the vicinity of the gamma detector assembly could lead to nontrivial variation in the random coincidence rate. This variation as well as the random coincidence contribution can be calibrated out of true coincidence event count using a delayed coincidence technique, well known to the art of positron imaging or measuring coincidence event count without any portion of imaging subject in the FOV.

Because of small volume contained in the FOV, almost all of the scatter coincidence events originate outside the FOV. Because the gamma detector pair represents such a small target on average for gammas originating outside the FOV the detection rate for the scatter coincidence events is negligible. The detection rate for true coincidence events strongly depends on the designs of the gamma detector assembly and individual gamma detector. Referring back to FIG. 4, for a given FOV defined by a cylindrical volumes 45 (shown in dotted line) of 0.6 cm in diameter bounded by two radiation sensitive faces 44A, 44B of a pair of gamma detectors 40, 47 and centered at the common symmetry axis of gamma detectors 40, 47 it is approximately 182 (counts/second)/($\mu$Ci/mL) and 319 (counts/second)/($\mu$Ci/mL) for a cylindrical FOV of 1 cm in diameter.

Cross talks between neighboring pixels is expected in the form of true coincidence events originating from neighboring pixels that fall into the geometric acceptance of the gamma detector assembly. The level of cross talk strongly depends on the geometry and radiation shielding arrangement of the gamma detector assembly and can be kept low through the optimization of these factors.

While preferred illustrative embodiments of the invention are described above, it will be apparent to those skilled in the art that various changes and modifications may be made therein without departing from the invention. Accordingly, the appended claims should be used to interpret the scope of the present invention.

What is claimed is:

1. A method for imaging a body part, the method comprising:
    providing at least a pair of gamma detectors disposed about and in an adjacent relationship with the body part, so as to detect coincident gamma ray pairs generated by positron annihilation events occurring within the body part, each detector capable of detecting gamma rays emitted by a positron emitting radiopharmaceutical infiltrated into the body part;
    scanning the detector pair over the body part;
    detecting coincident gamma ray pairs generated by positron annihilation events occurring within the body part at each scan interval;
    determining position coordinates of the detector pair with respect to a fixed origin at each scan interval; and
    utilizing the number of gamma ray pairs detected at each scan interval and the determined coordinates to generate an image indicative of the distribution of positron emitting radiopharmaceutical within the body part,
    wherein the gamma detectors are of dimensions suitable to be deployed inside a patient's digestive tract.

2. The method of claim 1, wherein the gamma detectors comprise scintillation crystals coupled to visible photon detectors.

3. The method of claim 2, wherein each scintillation crystal includes at least one selected from the group consisting of Cesium Iodide (CsI(Tl)), Bismuth Germinate (BGO), Lutetium Oxyorthosilicate (LSO), Lutetium Yttrium Orthosilicate (LYSO), Cerium-doped Gadolinium Silicate GSO, and Sodium Iodide (NaI(Tl)).

4. The method of claim 2, wherein each visible photon detector includes at least one selected from the group consisting of photomultiplier tube, silicon diode and avalanche photodiode.

5. The method of claim 1, wherein the gamma detectors comprise solid state gamma detectors.

6. The method of claim 5, wherein solid state gamma detectors are Cadmium Zinc Telluride (CZT), Cadmium Telluride (CdTe), Germanium (Ge), Silicon (Si), Mercuric Iodide (HgI), or a combination thereof.

7. The method of claim 1, wherein the gamma detectors are of position-sensitive type.

8. The method of claim 1, wherein each gamma detector has a transverse dimension of no more than 1.5 cm.

9. The method of claim 1, wherein each gamma detectors has a longitudinal dimension of no more than 2 cm.

10. The method of claim 1, wherein each gamma detector includes a radiation shielding component.

11. The method of claim 10, wherein the radiation shielding component includes tungsten, lead, molybdenum, or a combination thereof.

12. The method of claim 1, wherein the gamma detectors are scanned in raster pattern.

13. The method of claim 1, wherein the gamma detectors are scanned continuously.

14. A method for imaging a body part, the method comprising:
    providing at least a pair of gamma detectors disposed about and in an adjacent relationship with the body part, so as to detect coincident gamma ray pairs generated by positron annihilation events occurring within the body part, each detector capable of detecting gamma rays emitted by a positron emitting radiopharmaceutical infiltrated into the body part;
    scanning the detector pair over the body part;

detecting coincident gamma ray pairs generated by positron annihilation events occurring within the body part at each scan interval;

determining position coordinates of the detector pair with respect to a fixed origin at each scan interval; and utilizing the number of gamma ray pairs detected at each scan interval and the determined coordinates to generate an image indicative of the distribution of positron emitting radiopharmaceutical within the body part, wherein the body part is the wall of digestive tract including colon, stomach, esophagus, and small intestine.

15. A method for mapping a spatial distribution of a positron emitting radiopharmaceutical infiltrated into the body part, the method comprising:

providing a pair of detection means for detecting coincident gamma ray pairs emitted from positron annihilation events;

disposing the body part between the pair of detection means in opposing positional relationship with each other;

scanning the detection means across and over the body part while recording number of detected gamma ray pairs and position of the detection means; and generating a map representative of spatial distribution of radiopharmaceutical concentration within the body part, wherein the detection means is scanned in raster pattern.

16. The method of claim 15, wherein the detection means are selected from the group consisting scintillation detector, solid state gamma detector and position sensitive gamma detector.

17. The method of claim 15, wherein the detection means has radiation shielding means.

* * * * *